United States Patent
Kao et al.

(10) Patent No.: US 11,601,768 B2
(45) Date of Patent: Mar. 7, 2023

(54) METHOD OF GENERATING SOUNDS FOR REDUCING AN EFFECT OF TINNITUS AND TINNITUS CONTROL INSTRUMENT PERFORMING THE SAME

(71) Applicant: Airoha Technology Corp., Hsinchu (TW)

(72) Inventors: Kuo-Wei Kao, Taipei (TW); Neo Bob Chih-Yung Young, Taipei (TW); Kuo-Ping Yang, Taipei (TW)

(73) Assignee: AIROHA TECHNOLOGY CORP., Hsinchu (TW)

( * ) Notice: Subject to any disclaimer, the term of this patent is extended or adjusted under 35 U.S.C. 154(b) by 684 days.

(21) Appl. No.: 16/558,359

(22) Filed: Sep. 3, 2019

(65) Prior Publication Data
US 2020/0359143 A1   Nov. 12, 2020

(30) Foreign Application Priority Data

May 9, 2019 (TW) ................. 108116101

(51) Int. Cl.
 *H04R 25/00* (2006.01)
 *A61B 5/12* (2006.01)
 (Continued)

(52) U.S. Cl.
 CPC ............. *H04R 25/75* (2013.01); *A61B 5/128* (2013.01); *H04R 29/001* (2013.01); *A61F 11/00* (2013.01); *A61N 1/361* (2013.01); *A61N 1/36053* (2013.01)

(58) Field of Classification Search
 CPC .... A61N 1/361; A61N 1/36053; G09B 23/28; A61F 11/00; H04R 25/75; H04R 29/001; A61B 5/128
 See application file for complete search history.

(56) References Cited

U.S. PATENT DOCUMENTS

2004/0141624 A1* 7/2004 Davis .................... A61M 21/02
 600/25
2011/0071340 A1* 3/2011 Mcguire ............... A61M 21/00
 600/28
(Continued)

FOREIGN PATENT DOCUMENTS

AU   2004218727 A1   11/2004
CN   107041810 A      8/2017

OTHER PUBLICATIONS

University of California, Irvine, Low Pitch Treatment Alleviates Ringing sound of Tinnitus (Year: 2007).*

(Continued)

*Primary Examiner* — Matthew A Eason
*Assistant Examiner* — Kuassi A Ganmavo
(74) *Attorney, Agent, or Firm* — McClure, Qualey & Rodack, LLP

(57) ABSTRACT

A method of generating sounds for reducing an effect of tinnitus is disclosed. The method includes the following steps: acquiring a sound frequency of a tinnitus sound of a user, and playing a plurality of pure tones within a frequency range during a playback time, wherein the plurality of pure tones include a plurality of first pure tones and a plurality of second pure tones; the plurality of first pure tones and the sound frequency are located at a first frequency area, and the plurality of second pure tones are located at a second frequency area; the first frequency area covers X Hz, where $100 \leq X \leq 12000$, the second frequency area covers the remaining portion of the frequency range excluding the first frequency area, and the plurality of first pure tones accounts for M % of the plurality of pure tones, where $50 < M \leq 90$.

8 Claims, 3 Drawing Sheets

(51) Int. Cl.
    *H04R 29/00*     (2006.01)
    *A61N 1/36*     (2006.01)
    *A61F 11/00*     (2022.01)

(56) References Cited

U.S. PATENT DOCUMENTS

| | | | |
|---|---|---|---|
| 2013/0343581 A1* | 12/2013 | Dyrlund | H04R 25/75 381/312 |
| 2015/0050364 A1* | 2/2015 | Kang | A23L 33/105 424/725 |
| 2015/0051656 A1* | 2/2015 | Kilgard | A61N 1/36178 607/3 |
| 2015/0057360 A1* | 2/2015 | Guitton | A61K 31/135 514/647 |
| 2015/0164381 A1* | 6/2015 | Rush | A61B 5/128 381/73.1 |
| 2016/0089060 A1* | 3/2016 | Micheyl | A61B 5/72 600/559 |
| 2017/0027522 A1* | 2/2017 | Van Hasselt | H04R 25/00 |
| 2018/0325770 A1* | 11/2018 | Tass | A61H 23/00 |

OTHER PUBLICATIONS

Chinese language office action dated Jan. 13, 2022, issued in application No. CN 201910440278.3.
Chinese language office action dated Sep. 21, 2022, issued in application No. CN 201910440278.3.

\* cited by examiner

METHOD OF GENERATING SOUNDS FOR REDUCING AN EFFECT OF TINNITUS AND TINNITUS CONTROL INSTRUMENT PERFORMING THE SAME

BACKGROUND OF THE INVENTION

1. Field of the Invention

The present invention relates to a method of generating sounds for reducing an effect of tinnitus and a tinnitus control instrument performing the same; more particularly, the present invention relates to a method of generating sounds for reducing an effect of tinnitus by means of playing pure tones for a user to listen to, and a tinnitus control instrument for performing the method thereof.

2. Description of the Related Art

Tinnitus masking, which is a treatment for reducing tinnitus symptoms, can reduce the effects of loud tinnitus by means of playing sounds at a frequency close to the tinnitus frequency of a patient. However, a common tinnitus control instrument usually plays white noise or natural noise, which requires a louder volume and provides a relatively monotonous acoustic feeling to the patient, even though it can reduce the tinnitus symptoms.

Therefore, there is a need to provide a method of generating sounds for reducing an effect of tinnitus and a tinnitus control instrument performing the same to mitigate and/or obviate the aforementioned problems.

SUMMARY OF THE INVENTION

It is an object of the present invention to provide a method of playing pure tones for a user to listen in order to reduce an effect of tinnitus.

It is another object of the present invention to provide a tinnitus control instrument for performing the abovementioned method.

To achieve the abovementioned objects, the method of generating sounds for reducing an effect of tinnitus of the present invention is applied to a tinnitus control instrument. The tinnitus control instrument includes a speaker. In this invention, the method of generating sounds for reducing an effect of tinnitus comprises the following steps: acquiring a sound frequency of a tinnitus sound of a user; and controlling the speaker to play a plurality of pure tones within a frequency range during a playback time, wherein the plurality of pure tones include a plurality of first pure tones and a plurality of second pure tones; the sound frequency and the plurality of first pure tones are located at a first frequency area, and the plurality of second pure tones are located at a second frequency area; the first frequency area covers a range of X Hz, where $100 \leq X \leq 12000$, the second frequency area covers the remaining portion of the frequency range excluding the first frequency area, and the plurality of first pure tones account for M % of the plurality of pure tones, where $50 < M \leq 90$.

The tinnitus control instrument of the present invention comprises a speaker and a controller. The controller is electrically connected to the speaker and includes a tinnitus sound frequency acquisition module and a sound generation module. The tinnitus sound frequency acquisition module is used for acquiring a sound frequency of a tinnitus sound of a user. The sound generation module is used for controlling the speaker to play a plurality of pure tones within a frequency range during a playback time, wherein the plurality of pure tones include a plurality of first pure tones and a plurality of second pure tones; the sound frequency and the plurality of first pure tones are located at a first frequency area, and the plurality of second pure tones are located at a second frequency area; the first frequency area covers a range of X Hz, where $100 \leq X \leq 12000$, the second frequency area covers the remaining portion of the frequency range excluding the first frequency area, and the plurality of first pure tones account for M % of the plurality of pure tones, where $50 < M \leq 90$.

Other objects, advantages, and novel features of the invention will become more apparent from the following detailed description when taken in conjunction with the accompanying drawings.

BRIEF DESCRIPTION OF THE DRAWINGS

These and other objects and advantages of the present invention will become apparent from the following description of the accompanying drawings, which disclose several embodiments of the present invention. It is to be understood that the drawings are to be used for purposes of illustration only, and not as a definition of the invention.

In the drawings, wherein similar reference numerals denote similar elements throughout the several views.

DETAILED DESCRIPTION OF THE PREFERRED EMBODIMENT

Figure 1:
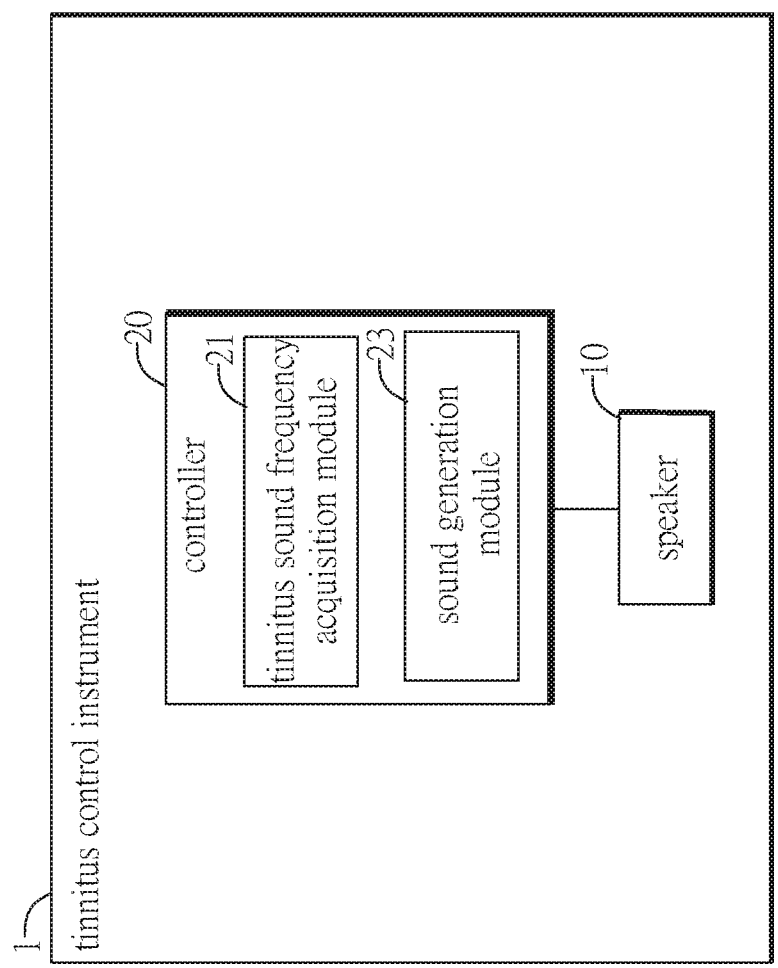
FIG. 1 illustrates a structural drawing of a tinnitus control instrument according to one embodiment of the present invention.

Please refer to FIG. 1, which illustrates a structural drawing of a tinnitus control instrument according to one embodiment of the present invention.

As shown in FIG. 1, in one embodiment of the present invention, the tinnitus control instrument 1 of the present invention is capable of playing sounds for reducing an effect of tinnitus of a user. The tinnitus control instrument 1 comprises a speaker 10 and a controller 20, wherein the controller 20 is electrically connected to the speaker 10. In one specific embodiment, the controller 20 can be a microcontroller, but the scope of the present invention is not limited to such. In one embodiment of the present invention, the controller 20 includes a tinnitus sound frequency acquisition module 21 and a sound generation module 23. Please note that the tinnitus sound frequency acquisition module 21 and the sound generation module 23 can be accomplished by hardware devices, software programs, firmware or combinations thereof and that they can also be configured in the form of circuit loops or other suitable formats; further, each of the modules can be configured either in an independent form or in a combined form. In one preferred embodiment, each of the modules is a software program stored in a storage unit (not shown in figures) of the controller 20, and a processing unit (not shown in figures) of the controller 20 will execute each module to achieve the purpose of the present invention. Moreover, the embodiment disclosed herein only describes a preferred embodiment of the present invention. To avoid redundant description, not all possible variations and combinations are described in detail in this specification. However, those skilled in the art will understand that the above modules or components are not all necessary pails, and that in order to implement the present invention, other more detailed known modules or components might also be included. It is possible that each module or component can be omitted or modified depending on different requirements, and it is also possible that other modules or components might be disposed between any two modules.

In one embodiment of the present invention, the tinnitus sound frequency acquisition module 21 is used for acquiring a sound frequency f of a tinnitus sound of a user. The process of acquiring the sound frequency of the tinnitus sound of the user will be disclosed in more detail hereinafter; therefore, there is no need for further description in this paragraph.

In one embodiment of the present invention, the sound generation module 23 is used for controlling the speaker 10 to play a plurality of pure tones within a frequency range during a playback time. The plurality of pure tones include a plurality of first pure tones and a plurality of second pure tones. The sound frequency f of the tinnitus sound of the user and the plurality of first pure tones are located at a first frequency area, and the plurality of second pure tones are located at a second frequency area. The first frequency area, covers a range of X Hz, where 100≤X≤12000, and the second frequency area covers the remaining portion of the frequency range excluding the first frequency area. The plurality of first pure tones account for M % of the plurality of pure tones, where 50<M≤90. That is, the number of the first pure tones being played is greater than that of the second pure tones. In one preferred embodiment of the present invention, the plurality of pure tones are generated randomly, and the probability of generating the first pure tones is 2 times the probability of generating the second pure tones. However, please note that the scope of the present invention is not limited to the above embodiment. The mechanism of determining the first frequency area and the second frequency area will be disclosed in more detail hereinafter; therefore, there is no need for further description in this paragraph.

Figure 2:
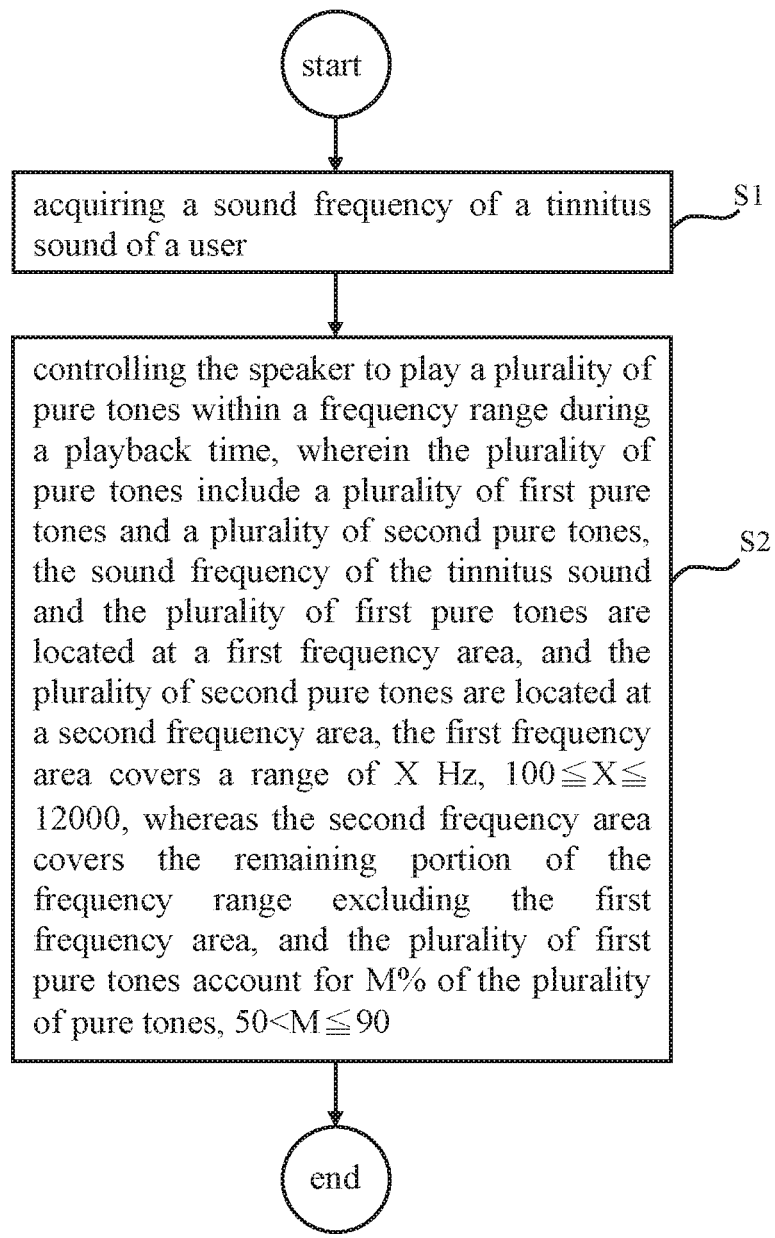
FIG. 2 illustrates a flowchart of a method of generating sounds for reducing an effect of tinnitus according to the present invention.
Figure 3:
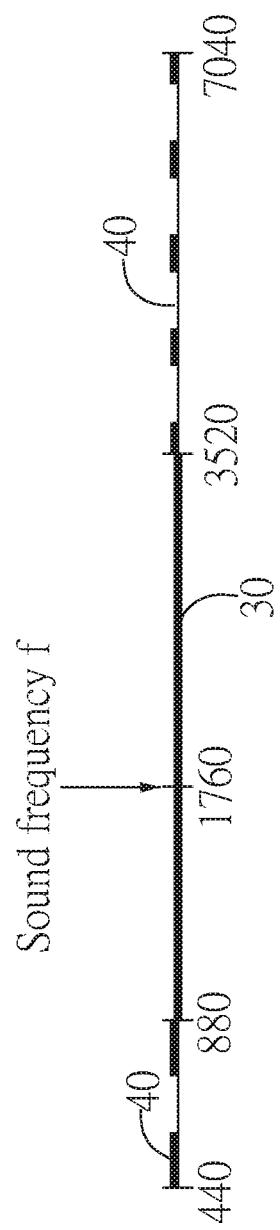
FIG. 3 illustrates a schematic drawing showing the frequency coverage of the first frequency area and the second frequency area according to the present invention.

Please refer to FIG. 1 to FIG. 3 altogether. FIG. 2 illustrates a flowchart of a method of generating sounds for reducing an effect of tinnitus according to the present invention, and FIG. 3 illustrates a schematic drawing showing the frequency coverage of the first frequency area and the second frequency area according to the present invention. The steps disclosed in FIG. 2 will be explained by referring to FIG. 1 and FIG. 3 in the following paragraph. Please note that the tinnitus control instrument 1 as shown in FIG. 1 is used as an example to explain the method of generating sounds for reducing an effect of tinnitus of the present invention; however, the method of generating sounds for reducing an effect of tinnitus of the present invention is not limited to application to a device having the same structure as the abovementioned tinnitus control instrument 1 only.

First, the method performs step S1: acquiring a sound frequency of a tinnitus sound of a user.

This step can be accomplished by means of a known tinnitus sound matching procedure. The tinnitus sound frequency acquisition module 21 will control the speaker 10 to play pure tones close to a tinnitus strength to a user having tinnitus symptoms and will request the user to press a specific (physical or virtual) button when the user feels the frequency of the pure tones is the same as or close to the tinnitus frequency in order to input a specific signal. At this time, the tinnitus sound frequency acquisition module 21 will use the frequency of the last pure tone prior to receiving the specific signal as the sound frequency f of the tinnitus sound.

Performing step S2: controlling the speaker to play a plurality of pure tones within a frequency range during a playback time, wherein the plurality of pure tones include a plurality of first pure tones and a plurality of second pure tones; the sound frequency of the tinnitus sound and the plurality of first pure tones are located at a first frequency area, and the plurality of second pure tones are located at a second frequency area; the first frequency area covers a range of X Hz, where 100≤X≤12000, the second frequency area covers the remaining portion of the frequency range excluding the first frequency area, and the plurality of first pure tones account for M % of the plurality of pure tones, where 50<M≤90.

After the sound frequency f of the tinnitus sound of the user is acquired, the user can then begin to use the tinnitus control instrument 1. When the user turns on the tinnitus control instrument 1, the sound generation module 23 can control the speaker 10 to play a plurality of pure tones within a frequency range during a playback time. The plurality of pure tones include a plurality of first pure tones and a plurality of second pure tones. The plurality of first pure tones and the sound frequency f of the tinnitus sound of the user are located at a first frequency area, and the plurality of second pure tones are located at a second frequency area. The first frequency area covers a range of X Hz, where 100≤X≤12000, and the second frequency area covers the remaining portion of the frequency range excluding the first frequency area. The plurality of first pure tones account for M % of the plurality of pure tones, where 50<M≤90. In one embodiment of the present invention, the frequency coverage of the first frequency area is dynamic; more precisely, the frequency band and the bandwidth covered by the first frequency area may vary according to the highs and lows of the sound frequency f of the tinnitus sound of the user.

In one embodiment of the present invention, if the acquired sound frequency f is Hz, the sound generation module 23 will define 0.25F-4F Hz as the abovementioned frequency range, and will define 0.5F-2F Hz as the first frequency area. The sound generation module 23 will also define the remaining portion of the frequency range excluding the first frequency area as the second frequency area, so the second frequency area will cover both ranges of 0.25 F-0.5 F Hz and 2 F-4 F Hz. Please refer to FIG. 3 as an example; if the acquired sound frequency f of the tinnitus sound of the user is 1760 Hz, the sound generation module 23 will define 440-7040 Hz as the frequency range, will define 880-3520 Hz as the first frequency area 30, and will define both 440-880 Hz and 3520-7040 Hz as the second frequency area 40. The sound generation module 23 can control the speaker 10 to randomly play a plurality of pure tones within the frequency range, and the probability of generating the pure tones located at the first frequency area 30 (i.e., the first pure tones) is 2 times the probability of generating the pure tones located at the second frequency area 40 (i.e., the second pure tones). That is, the number of the first pure tones being played is greater than that of the second pure tones.

In one embodiment of the present invention, the plurality of pure tones generated by the sound generation module 23 are tuned with 12-tone equal temperament. Furthermore, the plurality of pure tones located in the same octave are chord tones of the same chord. That is, the plurality of second pure tones having frequencies ranging from 0.25 F Hz to 0.5 F Hz are chord tones of the same chord, the plurality of first pure tones having frequencies ranging from 0.5 F Hz to F Hz are chord tones of the same chord, the plurality of first pure tones having frequencies ranging from F Hz to 2 F Hz are chord tones of the same chord, and the plurality of second pure tones having frequencies ranging from 2 F Hz to 4 F Hz are chord tones of the same chord. As a result, the pure tones being played have better musicality, thereby providing a better acoustic feeling to the user.

According to the abovementioned description, the method of generating sounds for reducing an effect of tinnitus and the tinnitus control instrument 1 of the present invention not only play pure tones at frequencies close to the tinnitus frequency hut also play pure tones at other frequencies which are not close to the tinnitus frequency, and such playback mechanism can effectively reduce the tinnitus symptoms at a relatively lower volume, as evidenced by experiments conducted by the inventor. Further, the method of generating sounds for reducing an effect of tinnitus and the tinnitus control instrument 1 of the present invention generate pure tones with a musical acoustic effect, which provides a better acoustic feeling to the user having tinnitus symptoms.

Please note that the abovementioned embodiment only describes a preferred embodiment of the present invention. To avoid redundant description, not all possible variations and combinations are described in detail in this specification. However, those skilled in the art will understand that the above modules or components are not all necessary parts, and that in order to implement the present invention, other more detailed known modules or components might also be included. It is possible that each module or component can be omitted or modified depending on different requirements, and it is also possible that other modules or components might be disposed between any two modules.

Although the present invention has been explained in relation to its preferred embodiments, it is to be understood that many other possible modifications and variations can be made without departing from the spirit and scope of the invention as hereinafter claimed.

What is claimed is:

1. A method of generating sounds for reducing an effect of tinnitus, applied to a tinnitus control instrument, wherein the tinnitus control instrument comprises a speaker, the method comprising the following steps:

acquiring a sound frequency of a tinnitus sound of a user; and controlling the speaker to play a plurality of pure tones within a frequency range during a playback time, wherein the plurality of pure tones comprises a plurality of first pure tones and a plurality of second pure tones; the sound frequency and the plurality of first pure tones are located at a first frequency area, and the plurality of second pure tones are located at a second frequency area; the first frequency area covers a range of X Hz, where $100 \leq X \leq 12000$, the second frequency area covers the remaining portion of the frequency range excluding the first frequency area, and the plurality of first pure tones account for M % of the plurality of pure tones, where $50 < M \leq 90$, wherein:

the sound frequency is F Hz, the frequency range covers from 0.25F Hz to 4F Hz, and the first frequency area covers from 0.5F Hz to 2F Hz, and the plurality of second pure tones having frequencies ranging from 0.25F Hz to 0.5F Hz are chord tones of the same chord, the plurality of first pure tones having frequencies ranging from 0.5F Hz to F Hz are chord tones of the same chord, the plurality of first pure tones having frequencies ranging from F Hz to 2F Hz are chord tones of the same chord, and the plurality of second pure tones having frequencies ranging from 2F Hz to 4F Hz are chord tones of the same chord.

2. The method as claimed in claim 1, wherein the frequencies of the plurality of pure tones are tuned with 12-tone equal temperament.

3. The method as claimed in claim 1, wherein the plurality of pure tones are generated randomly.

4. The method as claimed in claim 3, wherein the probability of generating the plurality of first pure tones is 2 times the probability of generating the plurality of second pure tones.

5. A tinnitus control instrument, used for playing a sound to reduce a tinnitus effect of a user, the tinnitus control instrument comprising:

a speaker; and a controller, electrically connected to the speaker, the controller comprising:

tinnitus sound frequency acquisition module, used for acquiring a sound frequency of a tinnitus sound of the user; and a sound generation module, used for controlling the speaker to play a plurality of pure tones within a frequency range during a playback time, wherein the plurality of pure tones comprise a plurality of first pure tones and a plurality of second pure tones; the sound frequency and the plurality of first pure tones are located at a first frequency area, and the plurality of second pure tones are located at a second frequency area; the first frequency area covers a range of X Hz, where $100 \leq X \leq 12000$, the second frequency area covers the remaining portion of the frequency range excluding the first frequency area, and the plurality of first pure tones account for M % of the plurality of pure tones, where $50 < M \leq 90$, wherein:

the sound frequency is F Hz, the frequency range covers from 0.25F Hz to 4F Hz, and the first frequency area covers from 0.5F Hz to 2F Hz, and the plurality of second pure tones having frequencies ranging from 0.25F Hz to 0.5F Hz are chord tones of the same chord, the plurality of first pure tones having frequencies ranging from 0.5F Hz to F Hz are chord tones of the same chord, the plurality of first pure tones having frequencies ranging from F Hz to 2F Hz are chord tones of the same chord, and the plurality of second pure tones having frequencies ranging from 2F Hz to 4F Hz are chord tones of the same chord.

6. The tinnitus control instrument as claimed in claim 5, wherein the frequencies of the plurality of pure tones are tuned with 12-tone equal temperament.

7. The tinnitus control instrument as claimed in claim 5, wherein the plurality of pure tones are generated randomly.

8. The tinnitus control instrument as claimed in claim 7, wherein the probability of generating the plurality of first pure tones is 2 times the probability of generating the plurality of second pure tones.

* * * * *